(12) United States Patent
Bowie et al.

(10) Patent No.: US 11,415,568 B2
(45) Date of Patent: Aug. 16, 2022

(54) SYSTEMS AND METHODS FOR IMPLICIT CHEMICAL RESOLUTION OF VACUUM GAS OILS AND FIT QUALITY DETERMINATION

(71) Applicant: ExxonMobil Technology and Engineering Company, Annandale, NJ (US)

(72) Inventors: Bryan T. Bowie, Branchburg, NJ (US); John E. Lee, Spring, TX (US); Bryan E. Hagee, Hamilton, NJ (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 393 days.

(21) Appl. No.: 16/565,608

(22) Filed: Sep. 10, 2019

(65) Prior Publication Data
US 2020/0103390 A1   Apr. 2, 2020

Related U.S. Application Data

(60) Provisional application No. 62/740,024, filed on Oct. 2, 2018.

(51) Int. Cl.
| | | |
|---|---|---|
| *G01N 21/00* | (2006.01) | |
| *G01N 33/28* | (2006.01) | |
| *G16C 20/30* | (2019.01) | |
| *G01J 3/453* | (2006.01) | |
| *G01N 21/35* | (2014.01) | |

(Continued)

(52) U.S. Cl.
CPC .......... *G01N 33/2829* (2013.01); *G01J 3/453* (2013.01); *G01N 21/35* (2013.01); *G06F 17/17* (2013.01); *G16C 20/30* (2019.02); *C10G 7/06* (2013.01); *C10G 2300/1059* (2013.01); *C10G 2300/302* (2013.01); *C10G 2300/308* (2013.01); *G06F 16/9035* (2019.01)

(58) Field of Classification Search
CPC .......... G01M 11/3145; G01M 11/335; G01M 11/33; G01M 11/3109; G01M 11/338
USPC ........................................................ 356/73.1
See application file for complete search history.

(56) References Cited

U.S. PATENT DOCUMENTS

| | | |
|---|---|---|
| 6,662,116 B2 | 12/2003 | Brown |
| 7,904,251 B2 | 3/2011 | Martin et al. |

(Continued)

FOREIGN PATENT DOCUMENTS

| | | |
|---|---|---|
| EP | 0726460 A2 | 8/1996 |

OTHER PUBLICATIONS

The International Search Report and Written Opinion of PCT/US2019/050284 dated Nov. 19, 2019.

(Continued)

*Primary Examiner* — Md M Rahman
(74) *Attorney, Agent, or Firm* — Vorys, Sater, Seymour and Pease LLP

(57) ABSTRACT

Systems and methods for implicit chemical resolution of vacuum gas oils and fit quality determination are disclosed. The systems and methods include utilizing an FT-IR spectrum of an unknown VGO composition, and a database of FT-IR spectra of known VGO compositions, to determine a model of composition for the unknown VGO composition. Additionally, the fit quality for the model of composition is determined by performing a partial least squares analysis on specific spectral regions of interest in the FT-IR spectrum of the unknown VGO composition.

20 Claims, 6 Drawing Sheets

(51) Int. Cl.
*G06F 17/17* (2006.01)
*G06F 16/9035* (2019.01)
*C10G 7/06* (2006.01)

(56) References Cited

U.S. PATENT DOCUMENTS

| | | |
|---|---|---|
| 8,322,200 B2 | 12/2012 | Brown et al. |
| 8,682,597 B2 | 3/2014 | Brown et al. |
| 2006/0047444 A1 | 3/2006 | Brown et al. |
| 2007/0212790 A1 | 9/2007 | Welch et al. |

OTHER PUBLICATIONS

Ghosh, et al., "Development of a Detailed Gasoline Composition-Based Octane Model", Ind. Eng. Chem. Res., 2006, vol. 45, pp. 337-345.
Ghosh, et al., "Detailed Composition-Based Model for Predicting the Cetane Number of Diesel Fuels", Ind. Eng Chem. Res., 2006, vol. 45, pp. 346-351.

SYSTEMS AND METHODS FOR IMPLICIT CHEMICAL RESOLUTION OF VACUUM GAS OILS AND FIT QUALITY DETERMINATION

CROSS REFERENCE TO RELATED APPLICATIONS

This application claims priority to U.S. Provisional Application Ser. No. 62/740,024 filed Oct. 2, 2018, which is herein incorporated by reference in its entirety.

FIELD

Systems and methods for implicit chemical resolution of vacuum gas oils via IR spectroscopy and fit quality determination of such implicit chemical resolution are provided.

BACKGROUND

Conventionally, various processes have been developed to model compositional properties of unknown petroleum distillate fractions, such as a vacuum gas oil (VGO) fraction. Certain processes can include lengthy analytical techniques that measure various bulk properties of an unknown sample and comparing these to known compositions to model various properties in the unknown sample, such as relative abundance (wt. %) of classes of compounds. Certain other processes can include the use of comparing multivariate analytical data of an unknown fraction, such as spectroscopic data, to multivariate analytical data of known compositions. It would be desirable to develop processes for modeling compositional properties that include providing reliable statistics to determine the quality of such modeling.

U.S. Pat. No. 6,662,116 describes a method of determining a property of an unknown material by fitting the infra-red (IR) spectrum of the unknown material to a linear combination of known IR spectra with known properties.

U.S. Pat. No. 7,904,251 describes a method for modifying a synthetically generated assay of a whole crude oil, such as a condensate or resid material, by using measured crude properties.

U.S. Pat. No. 8,322,200 describes a method of analyzing whether a manufactured product, e.g., a composition, meets regulatory and/or contractual requirements. The analysis is performed by re-introducing a manually or automatically collected sample that is representative of the manufactured product back into the one or more on-line process analyzers.

U.S. Pat. No. 8,682,597 describes a method for determining the composition of a material by fitting multivariate analytical data of an unknown whole crude to a database of multivariate analytical data of known whole crudes to provide an initial estimate of the composition. The method further includes refining the initial estimate of the composition by matching a set of additional analytical data.

SUMMARY

In one aspect, a method for estimating a composition for a vacuum gas oil (VGO) composition is provided. The method can include representing a FT-IR spectrum of a first VGO composition as a first weighted combination of FT-IR spectra from a database of FT-IR spectra. The method can also include generating a model of composition for the first VGO composition based on the first weighted combination of FT-IR spectra. The method can also include determining a first partial representation of the FT-IR spectrum of the first VGO composition as a second weighted combination of FT-IR spectra from the database of FT-IR spectra, the first partial representation being determined by partial least squares analysis. The first partial representation can correspond to one or more spectral regions associated with a first compositional class. The first partial representation can include a first leverage value and a first residual value. The method can further include determining a second partial representation of the FT-IR spectrum of the first VGO composition as a third weighted combination of FT-IR spectra from the database of FT-IR spectra, the second partial representation being determined by partial least squares analysis. The second partial representation can correspond to one or more spectral regions associated with a second compositional class. The second partial representation can include a second leverage value and a second residual value. Additionally, the method can include calculating a combined leverage value based on at least the first leverage value and the second leverage value. The method can also include calculating a combined residual value based on at least the first residual value and the second residual value. Further, the method can include identifying the first weighted combination of FT-IR spectra as having poor fit quality based on the combined leverage value being greater than one, the combined residual value being greater than one, or a combination thereof.

In another aspect, a method for estimating a composition for a vacuum gas oil (VGO) composition is provided. The method can include representing a FT-IR spectrum of a first VGO composition as a first weighted combination of FT-IR spectra from a database of FT-IR spectra. The method can also include generating a model of composition for the first VGO composition based on the first weighted combination of FT-IR spectra. The method can also include determining a first partial representation of the FT-IR spectrum of the first VGO composition as a second weighted combination of FT-IR spectra from the database of FT-IR spectra, the first partial representation being determined by partial least squares analysis. The first partial representation can correspond to a first spectral region that is associated with n-paraffins. The first partial representation can include a first leverage value and a first residual value. The method can further include determining a second partial representation of the FT-IR spectrum of the first VGO composition as a third weighted combination of FT-IR spectra from the database of FT-IR spectra, the second partial representation being determined by partial least squares analysis. The second partial representation can correspond to a second spectral region that is associated with naphthenes. The second partial representation can include a second leverage value and a second residual value. The method can also include calculating a combined leverage value based on at least the first leverage value and the second leverage value. Additionally, the method can include calculating a combined residual value based on at least the first residual value and the second residual value. Further, the method can include identifying the first weighted combination of FT-IR spectra as having poor fit quality based on the combined leverage value being greater than one, the combined residual value being greater than one, or a combination thereof.

In yet another aspect, a computerized system for chemical resolution of a vacuum gas oil (VGO) composition is provided. The system can include one or more processors; and non-transitory computer storage media storing computer-executable instructions that, when executed by the one or more processors, cause the one or more processors to perform a method. The method can include representing a FT-IR spectrum of a first VGO composition as a first weighted combination of FT-IR spectra from a database of FT-IR spectra. The method can further include generating a model of composition for the first VGO composition based on the first weighted combination of FT-IR spectra. The method can also include determining a first partial representation of the FT-IR spectrum of the first VGO composition as a second weighted combination of FT-IR spectra from the database of FT-IR spectra, the first partial representation being determined by partial least squares analysis. The first partial representation can correspond to one or more spectral regions associated with a first compositional class. The first partial representation can include a first leverage value and a first residual value. The method can also include determining a second partial representation of the FT-IR spectrum of the first VGO composition as a third weighted combination of FT-IR spectra from the database of FT-IR spectra, the second partial representation being determined by partial least squares analysis. The second partial representation can correspond to one or more spectral regions associated with a second compositional class. The second partial representation can include a second leverage value and a second residual value. The method can further include calculating a combined leverage value based on at least the first leverage value and the second leverage value. Additionally, the method can include calculating a combined residual value based on at least the first residual value and the second residual value. Further, the method can include identifying the first weighted combination of FT-IR spectra as having poor fit quality based on the combined leverage value being greater than one, the combined residual value being greater than one, or a combination thereof.

DETAILED DESCRIPTION

Overview

Figure 1:
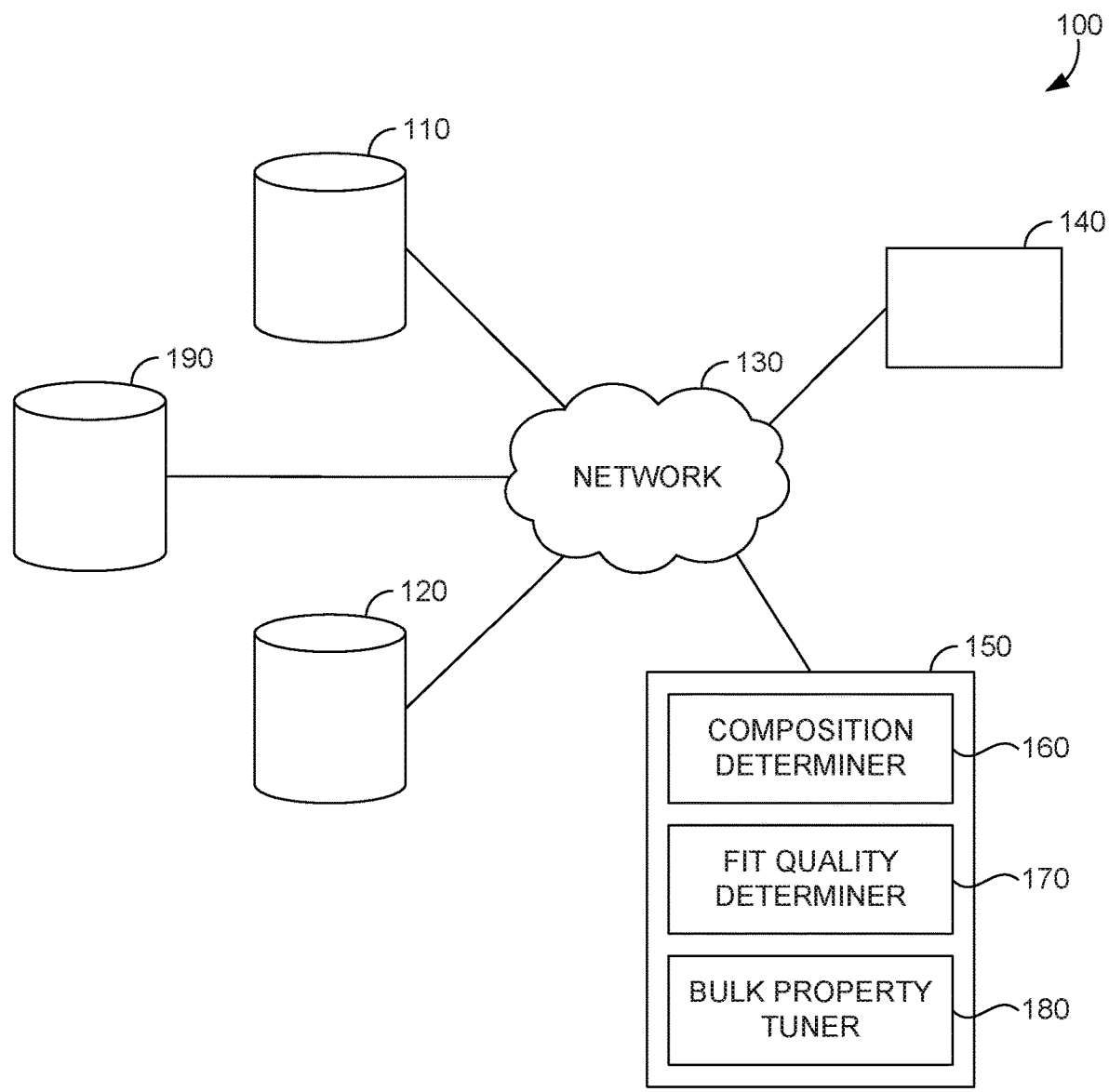
FIG. 1 shows a block diagram of a system for modeling a VGO composition.

In various aspects, systems and methods for estimating a composition for a VGO composition are provided. In aspects, the systems and methods can include determining a model of composition for the VGO composition based on a FT-IR spectrum of the VGO composition. In such aspects, the FT-IR spectrum from the VGO composition can be represented as a weighted combination of FT-IR spectra from a database of FT-IR spectra of known VGO compositions. This weighted combination of FT-IR spectra may then be utilized to generate a model of composition for the VGO composition. Further, in such aspects, a fit quality can be determined for this weighted combination of FT-IR spectra by determining one or more partial representations of the FT-IR spectrum of the VGO composition using a partial least squares analysis. In aspects, each of the partial representations can correspond to one or more spectral regions associated with a compositional class. In such aspects, combined leverage and combined residual values can be calculated based on these partial representations to discern if the weighted combination of FT-IR spectra is a good or poor fit.

Petroleum mixtures are made up of a large number of individual molecular components. These streams are complex and contain many distinct molecular species. As a result, efforts to describe the composition typically correspond to a model that provides a molecular approximation of the composition. Such a model may be used to simulate the physical and chemical transformations that occur in refinery processes, and to estimate the properties of the various petroleum feed and product streams. Analytical methods for approximating the detailed compositional profile of petroleum mixtures as a large, but finite, number of components already exist. For example, High Detailed Hydrocarbon Analysis (HDHA) is a protocol used in ExxonMobil to represent complex petroleum mixtures as an internally consistent set of components and is described in U.S. Pat. No. 8,682,597. The HDHA protocol for a petroleum mixture yields a compositional model, i.e., a model of composition.

Process and product property models (see for example Ghosh, P., Hickey, K. J., Jaffe, S. B., "Development of a Detailed Gasoline Composition-Based Octane Model", Ind. Eng. Chem. Res. 2006, 45, 227-345 and Ghosh, P., Jaffe, S. B., "Detailed Composition-Based Model for Predicting the Cetane Number of Diesel Fuels", Ind. Eng. Chem. Res. 2006, 45, 346-351) built on this model of composition are used in a large number of engineering and business applications such as plant optimization, raw materials acquisition, and process troubleshooting. Several of these stream properties are computed from correlations in which molecular-lump property densities take simple blending rules (e.g. linear) with respect to their wt % abundances in a stream's compositional model. However, development of detailed crude oil and plant stream analytical data to support these activities can be time consuming and expensive. The ability to estimate such compositions quickly and cheaply from limited amounts of measurements on any given sample would enhance the applicability and utility of these applications, reduce associated costs, and reduce R&D cycle times significantly. It would also facilitate development of on-line composition inference protocols that could be used to improve applications such as Real Time Optimization (RTO), and may have applicability to on-line blending.

A more rapid, less resource intensive process has been developed for providing a model of composition. For instance, a model of composition can be determined using (1) multivariate analytical techniques such as Fourier Transform Infrared Spectroscopy (FTIR) alone, or in combination with a small set of appropriately chosen property measurements of the sample whose composition is sought, (2) a library of similar samples that have measured multivariate analytical data (FTIR), measured HDHA and measured properties and (3) an optimization algorithm that constructs the reference composition for the sample as a blend of similar samples in the library so that the multivariate (FT-IR)

and property data for the blend is consistent with the multivariate (FT-IR) data and property made on that sample. The synthesis algorithm is then applied to adjust the reference composition to meet known properties of the unknown sample.

However, while such a method can estimate a model of composition for an unknown VGO sample, it is difficult to determine the fit quality of this prediction. For instance, in certain aspects, a model of composition, generated from a weighted combination of FT-IR spectra from known VGO compositions, does not indicate to an operator if this prediction has good fit quality for specific spectral regions of interest in the FT-IR spectrum of unknown VGO sample and/or for specific classes of compounds of interest in the unknown VGO sample.

The systems and methods disclosed herein can alleviate one or more of problems mentioned above. For example, in various aspects, the system and methods disclosed herein can provide a fit quality of the model of composition generated from a weighted combination of FT-IR spectra from known VGO compositions. In certain aspects, to determine the fit quality, one or more spectral regions of interest of the FT-IR spectrum of the unknown VGO composition, which may be associated with one or more compositional classes, are utilized to determine if such compositional classes are adequately represented in the database of FT-IR spectra of known VGO compositions. In such aspects, a weighted combination of FT-IR spectra from the database of known VGO compositions is utilized to determine a partial representation of the FT-IR spectral region of interest associated with a compositional class, e.g., n-paraffins, iso-paraffins, naphthenes, olefins, total aromatics, or one-, two-, three-, or four-ring aromatics. Further, in such aspects, a partial least squares analysis is performed to calculate a leverage and residual value for this partial representation, which may be utilized to determine the fit quality of the model of composition. In one aspect, a technical effect of the fit quality determination is to provide this indication of fit quality for the model of composition, so that the operator can rely on the model of composition for various subsequent processes.

In various aspects, the leverage and/or residual values of one or more of these spectral regions of interest (corresponding to one or more classes of compounds) can be weighted to give an increased level of importance to the overall analysis. For example, when determining the overall residual based on a plurality of compounds classes, a first compound class, such as n-paraffins, can be given increased weight while a second compound class, such as one-ring aromatics, can be given reduced weight. The cumulative error or weighted cumulative error statistics, e.g., leverage and/or residual values, generated from these specific models can be used to indicate the fit quality for the model of composition.

In certain aspects, a combined leverage of one or less and/or a combined residual of one or less can indicate that the model composition is a good fit. Since the operator can pick which spectral regions of interest for developing combined error statistics of the model of composition, an indication that such a model is a good fit provides an enhanced, more meaningful level of confidence in the model of composition.

In aspects where the model of composition is determined to be a good fit, the model of composition can be further refined or tuned with known bulk properties, such as density and/or API gravity.

A combined leverage above one or a combined residual above one may indicate that the model of composition is not a good fit. That is, such PLS statistical value(s) can indicate that the FT-IR spectral library of known compositions does not include adequate representation of spectral regions of interest (corresponding to classes of compounds of interest) in the FT-IR spectrum of the unknown VGO composition. For instance, if the residual or the leverage value is above one with respect to two-ring aromatic compounds and iso-paraffins, then the database of FT-IR spectra of known compositions does not adequately represent two-ring aromatic compounds and iso-paraffins. In such an instance, since the model of composition may not be a good fit, the operator may undergo other traditional bulk property analysis of the unknown sample in an attempt to better identify the composition of the unknown VGO sample.

In various aspects, reference may be made to one or more types of fractions generated during distillation of a petroleum feedstock. Such fractions may include a vacuum gas oil (VGO) fraction. The vacuum gas oil (VGO) fraction can be defined based on a boiling range. For instance, the VGO fraction can exhibit an initial or T5 boiling point of at least about 650° F. (343° C.), and a final or T95 boiling point of 1050° F. (566° C.). In this discussion, unless otherwise specified, "T5 boiling point" refers to a temperature at which 5 wt. % of the feed, effluent, product, stream, or composition of interest will boil. In this discussion, unless otherwise specified, "T95 boiling point" refers to a temperature at which 95 wt. % of the feed, effluent, product, stream, or composition of interest will boil.

Generation of a Model of Composition

In aspects, an unknown crude oil can be analyzed as a blend on known crude oils based on fitting the FT-IR spectrum of the unknown alone, or in combination with inspections such as API gravity and viscosity as a linear combination of spectra and inspections of reference crudes. Such a method can be used to estimate assay data for the unknown crude based on the calculated blend and the assay data of the reference crudes. Similarly, this method can be used to estimate a reference HDHA for the unknown crude based on the calculated blend and the measured HDHA of the reference crudes. The method can also be employed for analysis of petroleum feed and product streams, such as a VGO fraction. In an optional subsequent step, this reference HDHA can then be tuned to measured assay properties to yield an accurate estimate of the detailed composition of the unknown crude/stream. This method is described in detail in U.S. Pat. No. 6,662,116, the entire contents of which are incorporated herein by reference.

If the FT-IR spectrum is used alone, then the analysis may involve the minimization of the difference between the FT-IR spectrum of the unknown and that calculated as the linear combination of the FT-IR spectra of the blend of the reference samples. See equations (1) and (2) below.

$$\min((\hat{x}_u - x_u)^T (\hat{x}_u - x_u)) \tag{1}$$

$$\hat{x}_u = X c_u \tag{2}$$

$x_u$ is a column vector containing the FT-IR for the unknown crude, and X is the matrix of FT-IR spectra of the reference crudes. The FT-IR spectra are measured on a constant volume of crude oil, so they are blended on a volumetric basis. Both $x_u$ and X are orthogonalized to corrections (baseline polynomials, water vapor spectra, and liquid water spectra) as described in U.S. Pat. No. 6,662,116.

To ensure that the composition calculated is non-negative, the minimization is conveniently done using a non-negative least squares. The analysis provides coefficients for a linear combination of the reference crudes that most closely matches (in a least squares sense) the spectrum of the unknown crude.

Fit Quality Determination for the Predicted Model of Composition

As discussed above, in aspects, a model of composition, generated from a weighted combination of FT-IR spectra from known VGO compositions, does not indicate to an operator if this prediction has good fit quality for specific spectral regions of interest and/or for specific classes of compounds of interest. Rather, the fit parameters typically generated with such a model of composition relate to the entire spectrum, which may or may not be relevant to a specific spectral region of interest or for various compound classes of interest.

In aspects, to determine the fit quality, one or more spectral regions of interest of the FT-IR spectrum of the unknown VGO composition, which may be associated with one or more compositional classes, are utilized to determine if such compositional classes are adequately represented in the database of FT-IR spectra of known VGO compositions. In such aspects, a weighted combination of FT-IR spectra from the database of known VGO composition is utilized to determine a partial representation of the FT-IR spectral region of interest associated with a compositional class, e.g., n-paraffins, iso-paraffins, naphthenes, olefins, total aromatics, or one-, two-, three-, or four-ring aromatics. As discussed further below, in aspects, the resulting PLS values, e.g., combined leverage and/or combined residual, can be utilized to determine the fit quality for the model of composition.

As mentioned above, in various aspects, the specific spectral regions of interest can correlate with specific classes of compounds, e.g., n-paraffins, iso-paraffins, naphthenes, total aromatics, or one-, two-, three-, or four-ring aromatics. In one aspect, the n-paraffins can be associated with a wavelength region or regions of: about 1350 cm$^{-1}$ to about 1550 cm$^{-1}$, about 2750 cm$^{-1}$ to about 3000 cm$^{-1}$, about 4000 cm$^{-1}$ to about 4600 cm$^{-1}$, about 5400 cm$^{-1}$ to about 6000 cm$^{-1}$, or a combination thereof. In one aspect, the iso-paraffins can be associated with a wavelength region or regions of: about 900 cm$^{-1}$ to about 1200 cm$^{-1}$, about 1300 cm$^{-1}$ to about 1600 cm$^{-1}$, about 2600 cm$^{-1}$ to about 3000 cm$^{-1}$, about 4000 cm$^{-1}$ to about 4600 cm$^{-1}$, or a combination thereof. In various aspects, total naphthenes can be associated with a wavelength region or regions of: about 1450 cm$^{-1}$ to about 1550 cm$^{-1}$, about 2500 cm$^{-1}$ to about 3000 cm$^{-1}$, about 4000 cm$^{-1}$ to about 4600 cm$^{-1}$, or a combination thereof. In various aspects, total aromatics can be associated with a wavelength region or regions of: about 800 cm$^{-1}$ to about 1300 cm$^{-1}$, about 1450 cm$^{-1}$ to about 2000 cm$^{-1}$, about 3000 cm$^{-1}$ to about 3200 cm$^{-1}$, about 4000 cm$^{-1}$ to about 4600 cm$^{-1}$, or a combination thereof. In aspects, one-ring aromatics (ARC1) can be associated with a wavelength region or regions of: about 1450 cm$^{-1}$ to about 2000 cm$^{-1}$, about 3000 cm$^{-1}$ to about 3200 cm$^{-1}$, about 4000 cm$^{-1}$ to about 4600 cm$^{-1}$, or a combination thereof. In aspects, two-ring aromatics (ARC2) can be associated with a wavelength region or regions of: about 900 cm$^{-1}$ to about 1300 cm$^{-1}$, about 1550 cm$^{-1}$ to about 1750 cm$^{-1}$, about 2700 cm$^{-1}$ to about 3000 cm$^{-1}$, about 3000 cm$^{-1}$ to about 3200 cm$^{-1}$, or a combination thereof. In certain aspects, three-ring aromatics (ARC3) can be associated with a wavelength region or regions of: about 1000 cm$^{-1}$ to about 1100 cm$^{-1}$, about 1500 cm$^{-1}$ to about 1700 cm$^{-1}$, about 3000 cm$^{-1}$ to about 4500 cm$^{-1}$, or a combination thereof. In aspects, four-ring aromatics (ARC4) can be associated with a wavelength region or regions of: about 900 cm$^{-1}$ to about 1000 cm$^{-1}$, about 1100 cm$^{-1}$ to about 1200 cm$^{-1}$, about 1300 cm$^{-1}$ to about 1500 cm$^{-1}$, about 1650 cm$^{-1}$ to about 1850 cm$^{-1}$, about 3100 cm$^{-1}$ to about 3300 cm$^{-1}$, about 4100 cm$^{-1}$ to about 4400 cm$^{-1}$, or a combination thereof.

In various aspects, one or more spectral regions of interest (which correspond to classes of compounds) can be utilized in the fit quality determination. In such aspects, for each spectral region of interest, a weighted combination of FT-IR spectra from known VGO compositions is determined as a partial representation of the spectral region of interest. Further, as discussed above, a leverage and/or residual value can be determined for each of these partial representations. Leverage and/or residual values from two or more of these partial representations can be combined to determine a combined leverage value and/or a combined residual value, as described in the below PLS statistical equations.

In aspects, a conventional PLS model of combined residual ($FQR_{residual}$) can be utilized, such as that identified below in equation (3), in order to identify the combined difference between a fitted line and the corresponding data points from the spectral regions of interest in the unknown VGO spectrum.

$$FQR_{residual} = (R_{residual} * \mathbb{W}_{weights\ residual} * \mathbb{R}^T_{residual})/(90\%\ CI) \quad (3)$$

In this equation (3) the $\mathbb{R}_{residual}$ is as defined in equation (4) below, the $\mathbb{W}_{weights\ residual}$ is as defined in equation (5) below, and the residual is the transpose residual of equation (4). 90% CI refers to a 90% confidence interval.

In equation (4) below, the $\mathbb{R}_{residual}$ is a pooled value from the residuals determined for each spectral region of interest (corresponding to classes of compounds) of which a partial representation has been determined.

$$\mathbb{R}_{residual} = R_{n-p}, R_{i-p}, R_N, R_{ARC1}, R_{ARC2}, R_{ARC3}, R_{ARC4} \quad (4)$$

$R_{n-p}$ refers to the residual of the total n-paraffins, $R_{i-p}$ refers to the residual of the total iso-paraffins, $R_N$ refers to the residual of the total naphthenes, $R_{ARC1}$ refers to the residual of the one-ring aromatics, $R_{ARC2}$ refers to the residual of the two-ring aromatics, $R_{ARC3}$ refers to the residual of the three-ring aromatics, and $R_{ARC4}$ refers to the residual of the four-ring aromatics.

In equation (5) below, the individual $\mathbb{R}_{residual}$ values from equation (4) can be individually weighted to provide enhance importance to particular spectral regions of interest (corresponding to classes of compounds), as shown in equation (5) below.

$$\mathbb{W}_{weights\ residual} = \mathbb{W}r_{n-p}, \mathbb{W}r_{i-p}, \mathbb{W}r_N, \mathbb{W}r_{ARC1}, \mathbb{W}r_{ARC2}, \mathbb{W}r_{ARC3}, \mathbb{W}r_{ARC4} \quad (5)$$

$\mathbb{W}r_{n-p}$ refers to the weighted residual of the total n-paraffins, $\mathbb{W}r_{i-p}$ refers to the weighted residual of the total iso-paraffins, $Wr_N$ refers to the weighted residual of the total naphthenes, $\mathbb{W}r_{ARC1}$ refers to the weighted residual of the one-ring aromatics, $\mathbb{W}r_{ARC2}$ refers to the weighted residual of the two-ring aromatics, $\mathbb{W}r_{ARC3}$ refers to the weighted residual of the three-ring aromatics, and $\mathbb{W}r_{ARC4}$ refers to the weighted residual of the four-ring aromatics. In aspects, the residual of each individual class of compounds or spectral regions can be weighted differently from one another.

In aspects, a conventional PLS model of combined leverage ($FQR_{leverage}$) can be utilized, such as that identified below in equation (6), in order to provide a combined measure of data points from the sub-regions of interest in the unknown VGO spectrum that are outside the data points in the database of known VGO spectra.

$$FQR_{leverage}(L_{leverage} * W_{weights\ leverage} * L_{leverage}^T)/(90\%\ CI) \quad (6)$$

In this equation (6) the $L_{leverage}$ is as defined in equation (7) below, the $W_{weights\ leverage}$ is as defined in equation (8) below, and the $L_{leverage}^T$ is the transpose leverage of equation (7). 90% CI refers to a 90% confidence interval.

In equation 7 below, the $L_{leverage}$ is a pooled value from the leverage determined for each spectral region of interest (corresponding to classes of compounds) of which a partial representation has been determined.

$$L_{leverage} = L_{n-p}, L_{i-p}, L_N, L_{ARC1}, L_{ARC2}, L_{ARC3}, L_{ARC4} \quad (7)$$

$L_{n-p}$ refers to the leverage of the n-paraffins, $L_{i-p}$ refers to the leverage of the iso-paraffins, $L_N$ refers to the leverage of the naphthenes, $L_{ARC1}$ refers to the leverage of the one-ring aromatics, $L_{ARC2}$ refers to the leverage of the two-ring aromatics, $L_{ARC3}$ refers to the leverage of the three-ring aromatics, and $L_{ARC4}$ refers to the leverage of the four-ring aromatics.

In equation (8) below, the individual $L_{leverage}$ values from equation (7) can be individually weighted to provide enhance importance to particular spectral regions of interest (or classes of compounds of interest), as shown in equation (8) below.

$$W_{weights\ leverage} = W\ l_{n-p}, W\ l_{i-p}, W\ l_N, W\ l_{ARC1}, W\ l_{ARC2}, W\ l_{ARC3}, W\ l_{ARC4} \quad (8)$$

$W\ l_{n-p}$ refers to the weighted leverage of the n-paraffins, $Wl_{i-p}$ refers to the weighted leverage of the iso-paraffins, $W\ l_N$ refers to the weighted leverage of the naphthenes, $W\ l_{ARC1}$ refers to the weighted leverage of the one-ring aromatics, $W\ l_{ARC2}$ refers to the weighted leverage of the two-ring aromatics, $W\ l_{ARC3}$ refers to the weighted leverage of the three-ring aromatics, and $W\ l_{ARC4}$ refers to the weighted leverage of the four-ring aromatics. In aspects, the leverage of each individual class of compounds or spectral regions can be weighted differently from one another.

As discussed above, a combined residual ($FQR_{residual}$) of one or less and/or a combined leverage ($FQR_{leverage}$) of one or less can indicate that the model of composition is a good fit. Since the operator can pick which spectral regions of interest (corresponding to classes of compounds of interest) to develop combined error statistics for, an indication that such a model is a good fit provides an enhanced, more meaningful level of confidence in the model of composition. For example, in aspects, when the combined residual is one or less and/or the combined leverage is one or less, this can indicate that the model of composition is a good fit for the particular spectral regions of interest, or classes of compounds of interest; that is, that the database of FT-IR spectra of known VGO samples adequately represents the particular spectral regions of interest (or classes of compounds of interest) in the unknown VGO spectrum. In aspects where the model of composition is determined to be a good fit, the model of composition can be further refined or tuned with known bulk properties, such as API gravity and/or viscosity.

In various aspects, a combined leverage above one or a combined residual above one can indicate that the model of composition is not a good fit. That is, such PLS statistical value(s) can indicate that the database of FT-IR spectra of known compositions does not adequately represent spectral regions (corresponding to classes of compounds) of interest in the spectrum of the unknown VGO sample. For instance, if the residual or the leverage value is above one with respect to two-ring aromatic compounds and iso-paraffins, then the database of FT-IR spectra of known compositions does not include adequate representations of two-ring aromatic compounds and iso-paraffins. In such an instance, since the model of composition may not be a good fit, the operator may undergo other traditional bulk property chemical web lab testing of the unknown sample in an attempt to better identify the composition.

Optionally or alternatively, a distance PLS statistical value can be calculated to provide or refine fit quality information of the model of composition. A conventional PLS distance calculation is shown in equation (9) below.

$$D_{distance} = \sqrt{FQR_{residual}^2 + FQR_{leverage}^2} \quad (9)$$

As can be seen in equation (9), this distance calculation can provide a single statistical value that includes both the combined leverage and combined residual values discussed above. In this aspect, the single distance value can provide an alternative fit quality measurement which takes into account the relative strength of the combined leverage and combined residual. For example, by determining a single value fit quality, this allows an operator to determine if a favorable combined leverage, e.g., a value at or below one, can offset an unfavorable combined residual, e.g., a value above one. In another example, this single value distance analysis allows an operator to determine if a favorable combined residual, e.g., a value at or below one, can offset an unfavorable combined leverage, e.g., a value above one.

In certain aspects, the distance value itself can be utilized to determine the fit quality of the model of composition. In such aspects, if the distance value is about one or less, this can indicate that the fit quality is acceptable, whereas if the distance value is more than one, this can indicate that the fit quality is unacceptable.

Example System and Processes for Determining Fit Quality of a Model of Composition FIG. 1 is one example of a system 100 that can be utilized to determine the fit quality of a model of composition. It should be understood that the system 100 is an example of one suitable computing system environment and is not intended to suggest any limitation as to the scope of use or functionality of aspects of the present invention. Neither should the system 100 of FIG. 1 be interpreted as having any dependency or requirement related to any single source module, service, or device illustrated therein.

Generally, the system 100 can include a VGO composition modeler 150. The VGO composition modeler 150 can predict a model of composition of an unknown VGO sample using an FT-IR spectrum of the unknown sample, determine the fit quality of the model of composition, and optionally tune or refine the model of composition with known bulk properties.

The system 100 may include the VGO composition modeler 150, a known VGO spectra data source 110, compositional class data source 120, bulk property data source 190, and a computing device 140. In aspects, the VGO composition modeler 150, the known VGO spectra data source 110, the compositional class data source 120, the bulk property data source 190, and the computing device 140 all may be in communication with each other, through wired or wireless connections, and/or through a network 130. The network 130 may include, without limitation, one or more local area networks (LANs) and/or wide area networks (WANs). Such networking environments are commonplace in enterprise-wide computer networks, intranets, and the Internet. Accordingly, the network 130 is not further described.

In one or more aspects, the known VGO spectra data source 110 can include FT-IR spectra of known VGO samples. In such aspects, these known VGO samples can refer to VGO samples of measured compositions, e.g., known concentrations or relative amounts of various classes of compounds that make up the VGO sample.

In aspects, the compositional class data source 120 can include information on spectral regions of FT-IR spectra of one or more unknown VGO samples that may be of interest to an operator. In various aspects, the compositional class data source 120 can also include one or more FT-IR spectra of unknown VGO samples in order to identify specific spectral regions of interest for use in the fit quality determination. In one aspect, the compositional class data source 120 can include FT-IR spectral regions associated with n-paraffins, iso-paraffins, naphthenes, total aromatics, or one-, two-, three-, or four-ring aromatics, or combinations thereof. As discussed above, in one aspect, the n-paraffins can be associated with a wavelength region or regions of: about 1350 $cm^{-1}$ to about 1550 $cm^{-1}$, about 2750 $cm^{-1}$ to about 3000 $cm^{-1}$, about 4000 $cm^{-1}$ to about 4600 $cm^{-1}$, about 5400 $cm^{-1}$ to about 6000 $cm^{-1}$, or a combination thereof. In one aspect, the iso-paraffins can be associated with a wavelength region or regions of: about 900 $cm^{-1}$ to about 1200 $cm^{-1}$, about 1300 $cm^{-1}$ to about 1600 $cm^{-1}$, about 2600 $cm^{-1}$ to about 3000 $cm^{-1}$, about 4000 $cm^{-1}$ to about 4600 $cm^{-1}$, or a combination thereof. In various aspects, total naphthenes can be associated with a wavelength region or regions of: about 1450 $cm^{-1}$ to about 1550 $cm^{-1}$, about 2500 $cm^{-1}$ to about 3000 $cm^{-1}$, about 4000 $cm^{-1}$ to about 4600 $cm^{-1}$, or a combination thereof. In various aspects, total aromatics can be associated with a wavelength region or regions of: about 800 $cm^{-1}$ to about 1300 $cm^{-1}$, about 1450 $cm^{-1}$ to about 2000 $cm^{-1}$, about 3000 $cm^{-1}$ to about 3200 $cm^{-1}$, about 4000 $cm^{-1}$ to about 4600 $cm^{-1}$, or a combination thereof. In aspects, one-ring aromatics (ARC1) can be associated with a wavelength region or regions of: about 1450 $cm^{-1}$ to about 2000 $cm^{-1}$, about 3000 $cm^{-1}$ to about 3200 $cm^{-1}$, about 4000 $cm^{-1}$ to about 4600 $cm^{-1}$, or a combination thereof. In aspects, two-ring aromatics (ARC2) can be associated with a wavelength region or regions of: about 900 $cm^{-1}$ to about 1300 $cm^{-1}$, about 1550 $cm^{-1}$ to about 1750 $cm^{-1}$, about 2700 $cm^{-1}$ to about 3000 $cm^{-1}$, about 3000 $cm^{-1}$ to about 3200 $cm^{-1}$, or a combination thereof. In certain aspects, three-ring aromatics (ARC3) can be associated with a wavelength region or regions of: about 1000 $cm^{-1}$ to about 1100 $cm^{-1}$, about 1500 $cm^{-1}$ to about 1700 $cm^{-1}$, about 3000 $cm^{-1}$ to about 4500 $cm^{-1}$, or a combination thereof. In aspects, four-ring aromatics (ARC4) can be associated with a wavelength region or regions of: about 900 $cm^{-1}$ to about 1000 $cm^{-1}$, about 1100 $cm^{-1}$ to about 1200 $cm^{-1}$, about 1300 $cm^{-1}$ to about 1500 $cm^{-1}$, about 1650 $cm^{-1}$ to about 1850 $cm^{-1}$, about 3100 $cm^{-1}$ to about 3300 $cm^{-1}$, about 4100 $cm^{-1}$ to about 4400 $cm^{-1}$, or a combination thereof.

In various aspects, the bulk property data source 190 can include information on bulk properties of the known VGO compositions associated with the known VGO compositions in the known VGO spectra data source 110. In one or more aspects, the bulk properties can include API gravity, viscosity, distillation (or simulated distillation), sulfur content, nitrogen content, aliphatic sulfur content, basic nitrogen content, or combinations thereof.

In various aspects, the VGO composition modeler 150 can include a composition determiner 160, a fit quality determiner 170, and a bulk property tuner 180. In aspects, one or more of the composition determiner 160, a fit quality determiner 170, and a bulk property tuner 180 may be implemented as one or more stand-alone applications. Further, various services and/or modules may be located on any number of servers. By way of example only, VGO composition modeler 150 may reside on a server, cluster of servers, a cloud-computing device or distributed computing architecture, or a computing device remote from the known VGO spectra data source 110, the compositional class data source 120, the bulk property data source 190, and the computing device 140. In certain aspects, one or more services and/or modules of the VGO composition modeler 150 may reside in one or more of a computing device 140, such as a laptop computer, phone, and/or a tablet. In the same or alternative aspects, one or more services and/or modules of the VGO composition modeler 150 may reside in one or more servers, cluster of servers, cloud-computing devices or distributed computing architecture, or a computing device remote from the computing device 140.

In aspects, the composition determiner 160 can provide a model of composition. For instance, in such aspects, the composition determiner 160 receives or accesses an FT-IR spectrum for an unknown VGO sample, e.g., via the network 130, and receives the FT-IR spectra from the known VGO spectra data source 110. The composition determiner 160 determines a model of composition for the unknown VGO sample, e.g., using the process described above that involves representing the FT-IR spectrum of the unknown VGO sample as a weighted combination of FT-IR spectra of known VGO compositions and generating a model of composition from this representation. Further, in aspects, this can include determining the relative abundance (wt. %) values for various classes of compounds in the model of composition.

In aspects, the fit quality determiner 170 can determine the fit quality of the model of composition that was provided by the composition determiner 160. In various aspects, the fit quality determiner 170 receives or accesses spectral regions of interest of the FT-IR spectrum of the unknown VGO sample, e.g., from the compositional class data source 120. In aspects, an operator may indicate to the fit quality determiner 170 the specific spectral regions of interest, e.g., via the computing device 140. Further, the fit quality determiner 170 receives or accesses the FT-IR spectra from the known VGO spectra data source 110. The fit quality determiner 170 determines one or more of a combined leverage, a combined residual, and a distance as described in the PLS analysis above.

In various aspects, the bulk property tuner 180 can further refine the model of composition using bulk properties of the known VGO compositions utilized in forming the model of composition and/or bulk properties of unknown VGO composition.

In aspects, the VGO composition modeler 150 can provide to an operator, e.g., via the network 130, the model of composition and fit quality information as determined by one or more of the composition determiner 160, the fit quality determiner 170, and the bulk property tuner 180.

Figure 2:
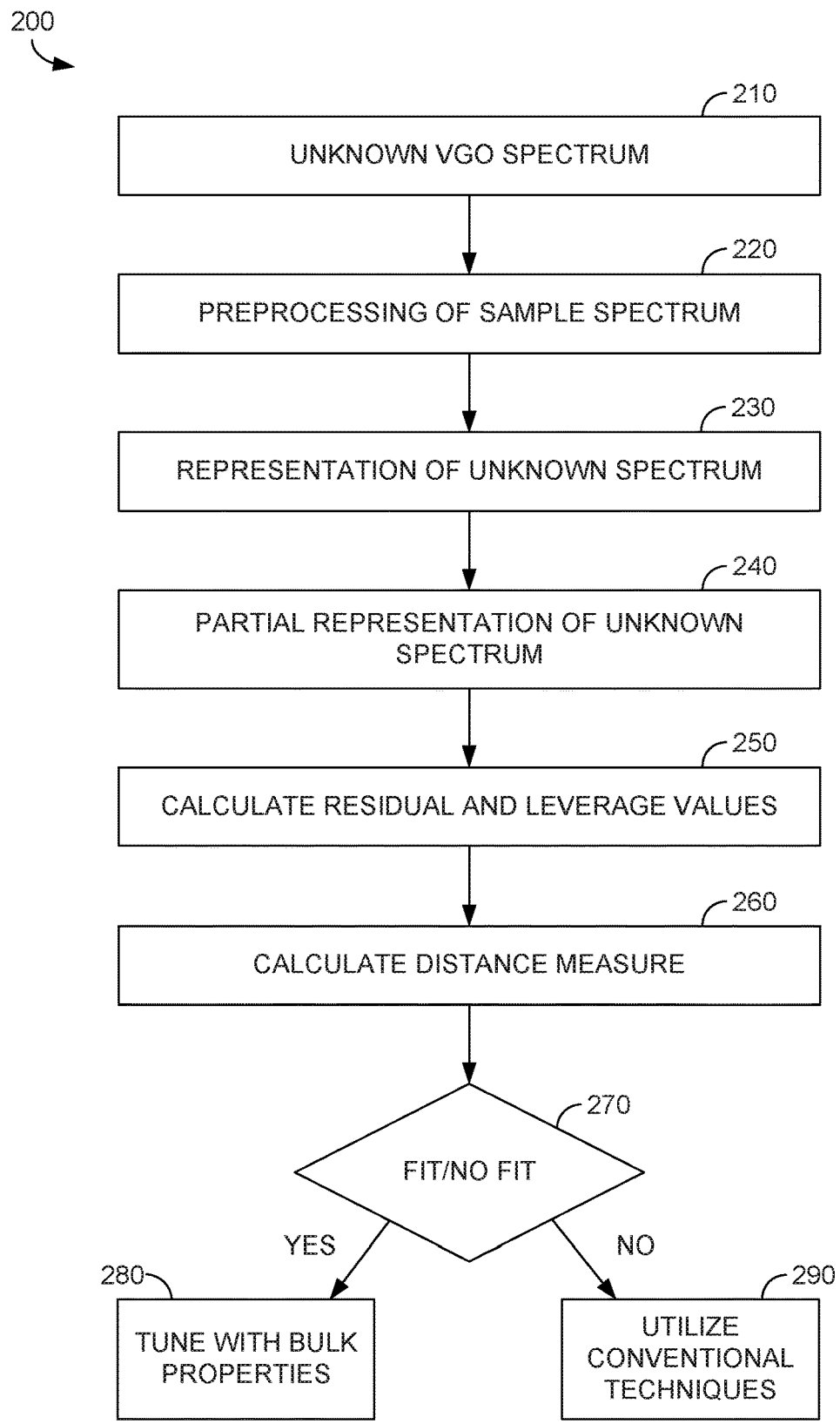
FIG. 2 shows a flow diagram illustrating processes for determining a VGO composition.

Turning now to FIG. 2, a flow diagram illustrating various processes for modeling a VGO composition is illustrated. The process 200 starts with the step 210 of obtaining an FT-IR spectrum of the unknown VGO sample. Any convenient method for obtaining an FT-IR spectrum of the unknown VGO sample can be utilized.

In step 220, the FT-IR spectrum of the unknown VGO composition can be preprocessed. In such aspects, the preprocessing can include trimming the FT-IR spectrum into spectral regions of interest that can be utilized in fit quality determinations discussed herein. In one aspect, the FT-IR spectrum can be trimmed into regions that correspond to classes of compounds of interest, such as n-paraffins, iso-paraffins, naphthenes, total aromatics, one-ring aromatics, two-ring aromatics, three-ring aromatics, and four-ring aromatics.

In step 230, the FT-IR spectrum of the unknown VGO sample is represented as a weighted combination of FT-IR spectra from a database of FT-IR spectra of known VGO compositions. In aspects, the step 230 includes the processes described in detail above that relates to generating a model of composition. As described above, based on the weighted combination of FT-IR spectra of known VGO samples, a model of composition is generated. In aspects, since the compositional profile of the VGO compositions from the database may be known, such as relative abundance (wt. %) of various classes of compounds, the model of composition can include the relative abundance of specific classes of compounds, such as paraffins, naphthenes, and aromatics.

In step 240, partial representations of spectral regions of interest (of the FT-IR spectrum of the unknown VGO sample) are determined. These partial representations of interest include a weighted combination of FT-IR spectra of known VGO compositions. In aspects, the step 240 includes the processes described in detail above for determining the fit quality of the model of composition. In one aspect, the spectral regions of interest can correlate to one or more classes of compounds, as discussed above. This step 240 (along with steps 250, 260, and 270) provides for a targeted query of the database of FT-IR spectra of known VGO samples to determine if classes of compounds of interest are adequately represented so that the model of composition (determined in step 230) can be indicated as a reliable, quality fit, or not.

In step 250, the residual and leverage values are determined for the partial representations of spectral regions of interest determined in step 240. In one aspect, the residual and leverage values can be determined according to the equations (3)-(8) discussed in detail above.

In step 260, a distance measure is calculated based on the residual and leverage values calculated in step 250. The distance measure can be determined utilizing the equation (9) discussed in detail above.

In step 270, a determination is made as to whether or not the model of composition is a good fit or not. In one aspect, a combined residual ($FQR_{residual}$) of one or less and/or a combined leverage ($FQR_{leverage}$) of one or less indicates that the model composition is a good fit. In the same or alternative aspects, when the distance measure is above one, the model of composition is determined to be a bad fit.

It should be understood that the determination of the model of composition in step 230 can be performed concurrent to the steps 240-270 that determine the fit quality of the model of composition.

In step 280, in aspects where the model of composition is determined to be a good fit, the model of composition can be further refined or tuned with known bulk properties, such as API gravity and/or viscosity as discussed above.

In step 290, in aspects where the model of composition is determined to not be a good fit, further conventional assay techniques can be utilized to develop a composition profile for the unknown VGO sample, such as gas chromatography, liquid chromatography, and/or NMR.

Example—Comparison of the Inventive Process to a Conventional Process

This Example provides a comparison of: 1) predicted values for relative amounts (wt. %) of specific compositional classes for various VGO samples as determined by the processes discussed above; 2) predicted values for relative amounts (wt. %) of specific compositional classes for various VGO samples as determined by the CRUDESUITE™ model; and 3) the measured amounts of these classes of compounds in the various VGO samples. The VGO samples utilized in this Example did not have measured HDHA values.

Using the processes described above, an FT-IR spectrum is obtained on a VGO sample, and a model of composition is determined, which includes a relative amount (wt. % of the VGO) of the following compositional classes: normal paraffins (n-paraffins); iso-paraffins; naphthenes; and total aromatics. Further, using the processes described above, a PLS analysis is performed to determine a fit quality of the model of composition is. If the fit quality is poor (combined residual is above 1 and combined leverage is above 1) the model of composition is not utilized for further analysis in this Example.

As noted above, the various VGO samples are also analyzed by a commercially available modeling software (CRUDESUITE™) by Spiral Solutions. The CRUDESUITE™ model uses minimal bulk properties to determine compositional properties of the VGO sample.

Further, the various VGO samples were analyzed using conventional techniques to perform actual measurements on the amounts of the specific compositional classes.

Figure 3:
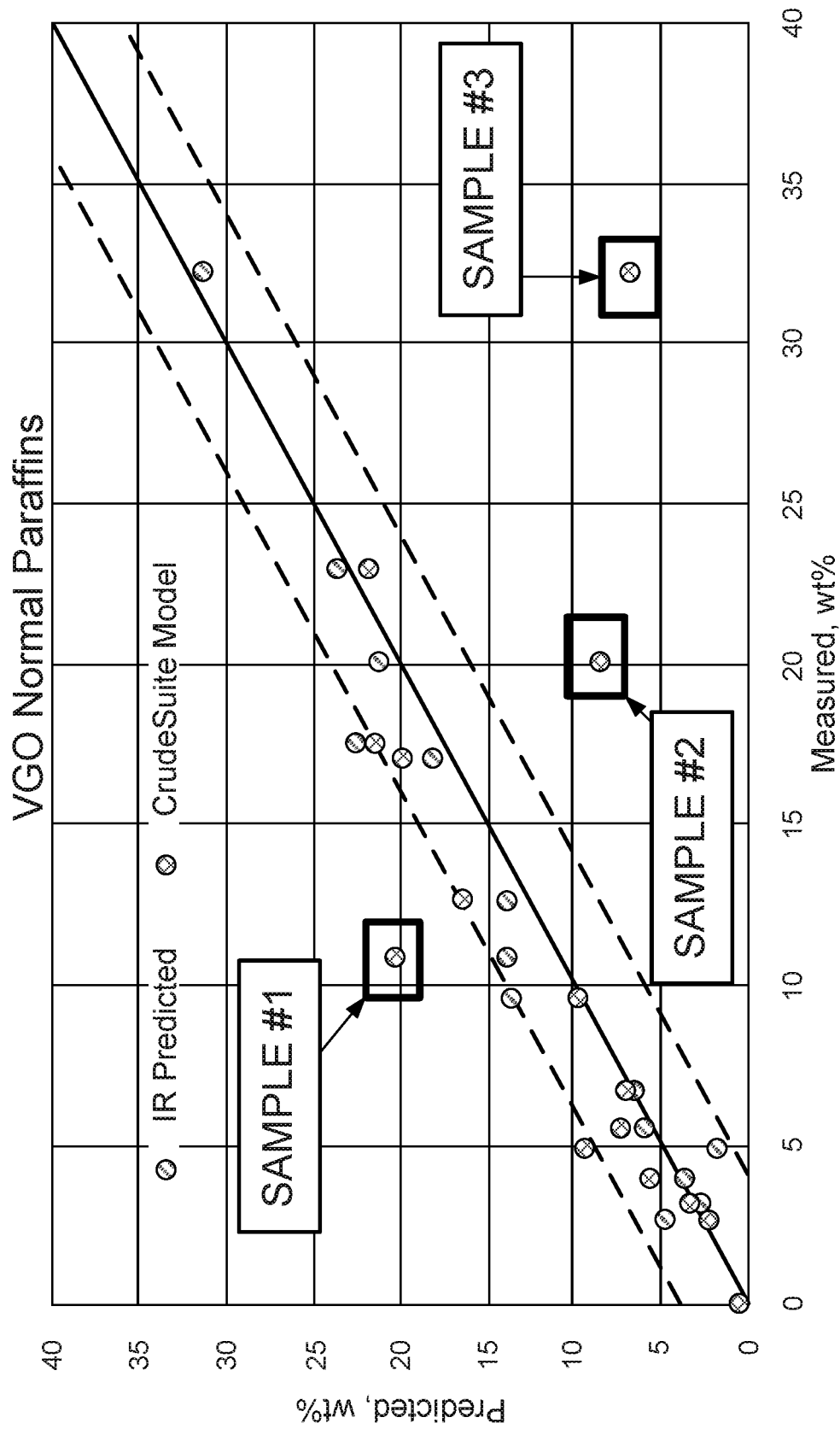
FIG. 3 shows a graph illustrating the measured amount of n-paraffins in various VGO samples compared to the predicted amount of n-paraffins using the inventive method and a commercial method.

FIG. 3 shows a graph with the measured amount (wt. %) of n-paraffins (x-axis) and the predicted amount (wt. %) of n-paraffins (y-axis) for various VGO samples that were modeled by the inventive processes and the CRUDESUITE™ model. As can be seen in FIG. 3, the inventive processes resulted in the plotted data points hovering around parity (where the predicted wt. %=the measured wt. %) with only one outlier data point being outside +/−4% of parity. In contrast, the CRUDESUITE™ model resulted in three outlier data points being substantially outside of +/−4% of parity. As can be seen in FIG. 3, the CRUDESUITE™ model underestimated the amount of n-paraffins for two of the VGO samples (Sample 2 and Sample 3), and overestimated the amount of n-paraffins for one of the VGO samples (Sample 1).

Figure 4:
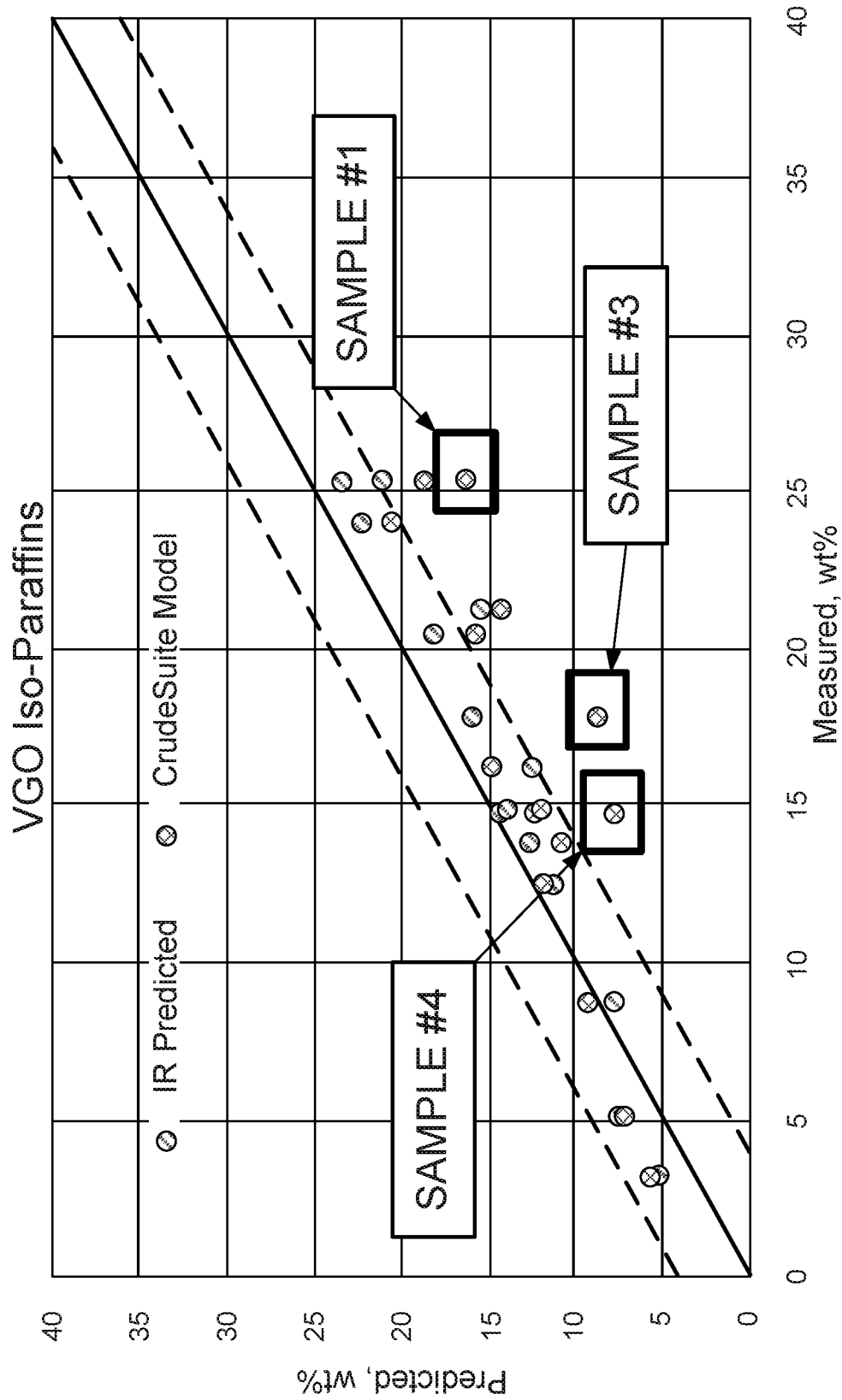
FIG. 4 shows a graph illustrating the measured amount of iso-paraffins in various VGO samples compared to the predicted amount of iso-paraffins using the inventive method and a commercial method.

FIG. 4 shows a graph with the measured amount (wt. %) of iso-paraffins (x-axis) and the predicted amount (wt. %) of iso-paraffins (y-axis) for various VGO samples that were modeled by the inventive processes and the CRUDESUITE™ model. As can be seen in FIG. 4, while overall the trend was for both the inventive processes and the CRUDESUITE™ model to underestimate the amount of iso-paraffins, only the CRUDESUITE™ model substantially underestimated the amount of iso-paraffins in six VGO samples, with six data points outside of −4% of parity.

Figure 5:
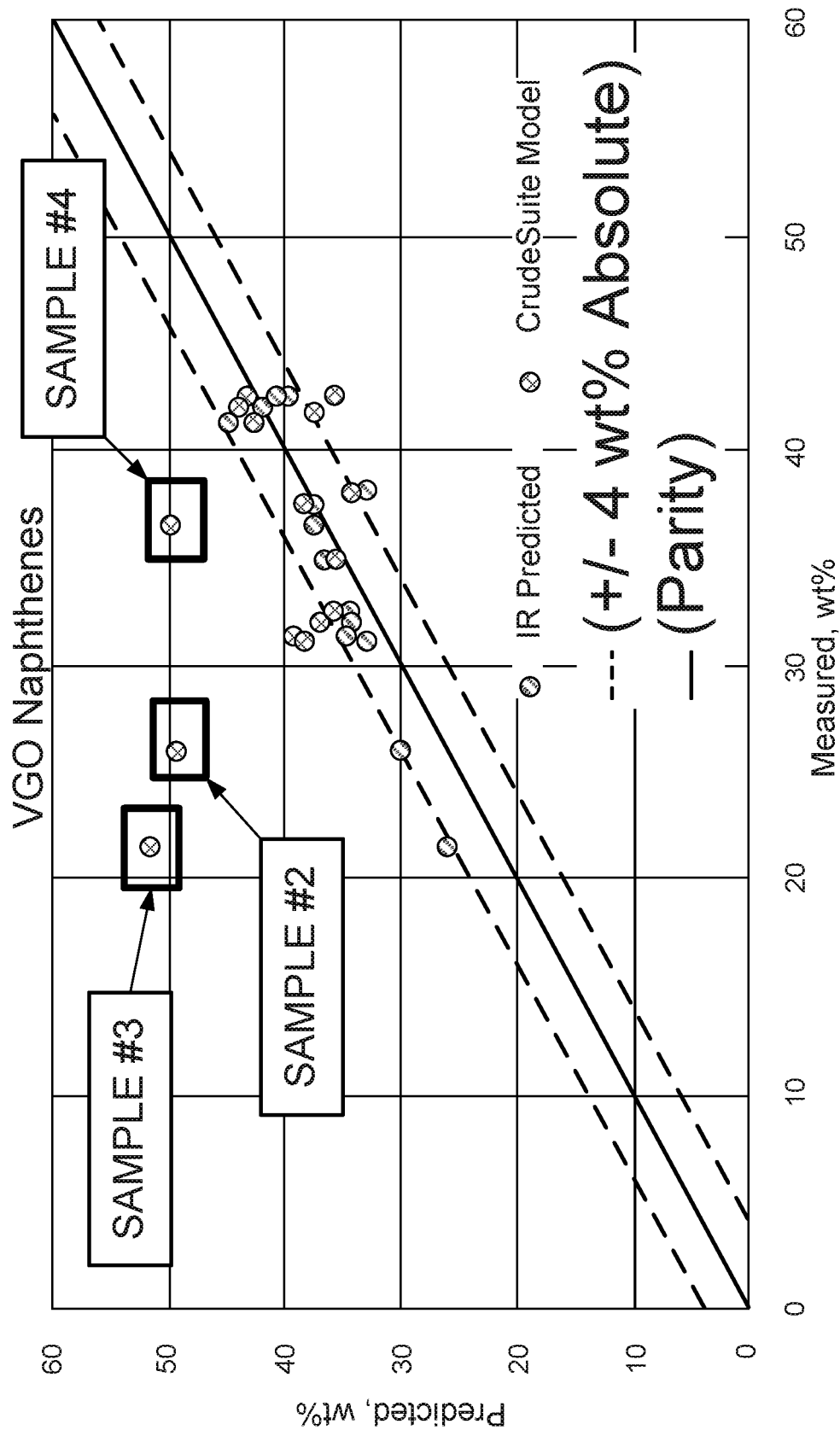
FIG. 5 shows a graph illustrating the measured amount of naphthenes in various VGO samples compared to the predicted amount of naphthenes using the inventive method and a commercial method.

FIG. 5 shows a graph with the measured amount (wt. %) of naphthenes (x-axis) and the predicted amount (wt. %) of naphthenes (y-axis) for various VGO samples that were modeled by the inventive processes and the CRUDESUITE™ model. As can be seen in FIG. 5, while overall the trend was for both the inventive processes and the CRUDESUITE™ model to generally estimate well the amount of naphthenes, only the CRUDESUITE™ model substantially overestimated the amount of naphthenes in three VGO samples, with three data points substantially outside of +4% of parity (Samples 2, 3, and 4).

Figure 6:
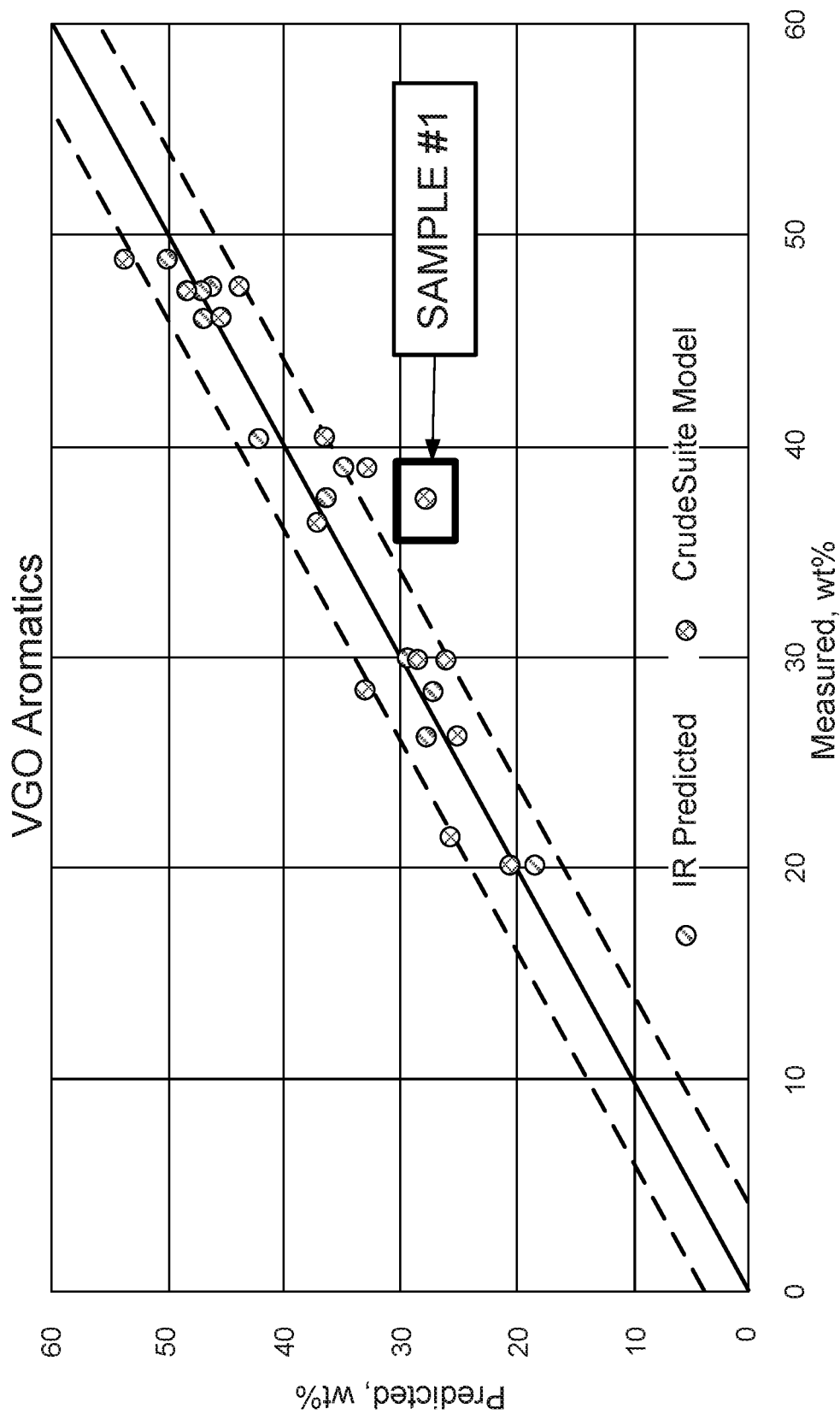
FIG. 6 shows a graph illustrating the measured amount of aromatics in various VGO samples compared to the predicted amount of aromatics using the inventive method and a commercial method.

FIG. 6 shows a graph with the measured amount (wt. %) of aromatics (x-axis) and the predicted amount (wt. %) of aromatics (y-axis) for various VGO samples that were modeled by the inventive processes and the CRUDESUITE™ model. As can be seen in FIG. 6, while overall the trend was for both the inventive processes and the CRUDESUITE™ model to generally estimate well the amount of aromatics, only the CRUDESUITE™ model substantially underestimated the amount of aromatics in two VGO samples, with two data points substantially outside of −4% of parity.

Additional Embodiments

Embodiment 1. A method for estimating a composition for a vacuum gas oil (VGO) composition, comprising: representing a FT-IR spectrum of a first VGO composition as a first weighted combination of FT-IR spectra from a database of FT-IR spectra; generating a model of composition for the first VGO composition based on the first weighted combination of FT-IR spectra; determining a first partial representation of the FT-IR spectrum of the first VGO composition as a second weighted combination of FT-IR spectra from the database of FT-IR spectra, the first partial representation being determined by partial least squares analysis, wherein the first partial representation corresponds to one or more spectral regions associated with a first compositional class, and wherein the first partial representation comprises a first leverage value and a first residual value; determining a second partial representation of the FT-IR spectrum of the first VGO composition as a third weighted combination of FT-IR spectra from the database of FT-IR spectra, the second partial representation being determined by partial least squares analysis, wherein the second partial representation corresponds to one or more spectral regions associated with a second compositional class, and wherein the second partial representation comprises a second leverage value and a second residual value; calculating a combined leverage value based on at least the first leverage value and the second leverage value; calculating a combined residual value based on at least the first residual value and the second residual value; identifying the first weighted combination of FT-IR spectra as having poor fit quality based on the combined leverage value being greater than one, the combined residual value being greater than one, or a combination thereof.

Embodiment 2. The method of embodiment 1, wherein the first compositional class comprises n-paraffins; or wherein the second compositional class comprises naphthenes; or a combination thereof.

Embodiment 3. The method of any of embodiments 1-2, wherein the first weighted combination corresponds to a linear combination of FT-IR spectra from the database of FT-IR spectra.

Embodiment 4. The method of any of embodiments 1-3, further comprising: determining a third partial representation of the FT-IR spectrum of the first VGO composition as a fourth weighted combination of FT-IR spectra from the database of FT-IR spectra, the third partial representation being determined by partial least squares analysis, wherein the third partial representation corresponds to one or more spectral regions associated with a third compositional class, and wherein the third partial representation comprises a third leverage value and a third residual value.

Embodiment 5. The method of embodiment 4, wherein the third compositional class is selected from: iso-paraffins; aromatics; one-ring aromatics; two-ring aromatics: three-ring aromatics: or four-ring aromatics.

Embodiment 6. The method of any of embodiments 1-5, wherein the first VGO composition has an initial or T5 boiling point of at least about 650° F. (343° C.) and a final or T95 boiling point of 1050° F. (566° C.).

Embodiment 7. The method of any of embodiments 1-6, wherein at least a portion of the generating a model of composition for the first VGO composition and at least a portion of the identifying the first weighted combination of FT-IR spectra as having poor fit quality occur concurrently.

Embodiment 8. The method of any of embodiments 1 and 3-7, wherein the first compositional class and the second compositional class are selected from: n-paraffins; iso-paraffins; naphthenes; olefins; total aromatics; one-ring aromatics; two-ring aromatics; three-ring aromatics; four-ring aromatics or a combination thereof, and wherein the first compositional class and the second compositional class are different from one another.

Embodiment 9. The method of any of embodiments 1-8, wherein the one or more spectral regions of the first partial representation and the one or more spectral regions of the second partial representation are selected from: 1) about 1350 $cm^{-1}$ to about 1550 $cm^{-1}$, about 2750 $cm^{-1}$ to about 3000 $cm^{-1}$, about 4000 $cm^{-1}$ to about 4600 $cm^{-1}$, about 5400 $cm^{-1}$ to about 6000 $cm^{-1}$, or a combination thereof; 2) about 900 $cm^{-1}$ to about 1200 $cm^{-1}$, about 1300 $cm^{-1}$ to about 1600 $cm^{-1}$, about 2600 $cm^{-1}$ to about 3000 $cm^{-1}$, about 4000 $cm^{-1}$ to about 4600 $cm^{-1}$, or a combination thereof; 3) about 1450 $cm^{-1}$ to about 1550 $cm^{-1}$, about 2500 $cm^{-1}$ to about 3000 $cm^{-1}$, about 4000 $cm^{-1}$ to about 4600 $cm^{-1}$, or a combination thereof; 4) about 800 $cm^{-1}$ to about 1300 $cm^{-1}$, about 1450 $cm^{-1}$ to about 2000 $cm^{-1}$, about 3000 $cm^{-1}$ to about 3200 $cm^{-1}$, about 4000 $cm^{-1}$ to about 4600 $cm^{-1}$, or a combination thereof; 5) about 1450 $cm^{-1}$ to about 2000 $cm^{-1}$, about 3000 $cm^{-1}$ to about 3200 $cm^{-1}$, about 4000 $cm^{-1}$ to about 4600 $cm^{-1}$, or a combination thereof; 6) about 900 $cm^{-1}$ to about 1300 $cm^{-1}$, about 1550 $cm^{-1}$ to about 1750 $cm^{-1}$, about 2700 $cm^{-1}$ to about 3000 $cm^{-1}$, about 3000 $cm^{-1}$ to about 3200 $cm^{-1}$, or a combination thereof; 7) about 1000 $cm^{-1}$ to about 1100 $cm^{-1}$, about 1500 $cm^{-1}$ to about 1700 $cm^{-1}$, about 3000 $cm^{-1}$ to about 4500 $cm^{-1}$, or a combination thereof; or 8) about 900 $cm^{-1}$ to about 1000 $cm^{-1}$, about 1100 $cm^{-1}$ to about 1200 $cm^{-1}$, about 1300 $cm^{-1}$ to about 1500 $cm^{-1}$, about 1650 $cm^{-1}$ to about 1850 $cm^{-1}$, about 3100 $cm^{-1}$ to about 3300 $cm^{-1}$, about 4100 $cm^{-1}$ to about 4400 $cm^{-1}$, or a combination thereof.

Embodiment 10. The method of embodiment 2, wherein the first spectral region associated with n-paraffins comprises a wavelength region or regions of: about 1350 $cm^{-1}$ to about 1550 $cm^{-1}$, about 2750 $cm^{-1}$ to about 3000 $cm^{-1}$, about 4000 $cm^{-1}$ to about 4600 $cm^{-1}$, about 5400 $cm^{-1}$ to about 6000 $cm^{-1}$, or a combination thereof.

Embodiment 11. The method of embodiment 2, wherein the second spectral region associated with naphthenes comprises a wavelength region or regions of: about 1450 $cm^{-1}$ to about 1550 $cm^{-1}$, about 2500 $cm^{-1}$ to about 3000 $cm^{-1}$, about 4000 $cm^{-1}$ to about 4600 $cm^{-1}$, or a combination thereof.

Embodiment 12. The method of any of embodiments 1-11, wherein the identifying to the first weighted combination of FT-IR spectra as having poor fit quality is based on the combined leverage value being greater than one and the combined residual value being greater than one.

Embodiment 13. The method of any of embodiments 1-12, wherein the model of composition for the first VGO composition comprises a relative abundance (wt. %) of one or more classes of compounds, the one or more classes of compounds comprising n-paraffins, iso-paraffins, naphthenes, aromatics, one-ring aromatics, two-ring aromatics, three-ring aromatics, and four-ring aromatics.

Embodiment 14. The method of any of embodiments 1-13, further comprising tuning the model of composition with one or more bulk properties, the one or more bulk properties comprising API gravity, viscosity, distillation temperatures, simulated distillation temperatures, sulfur content, nitrogen content, aliphatic sulfur content, basic nitrogen content, or combinations thereof.

Embodiment 15. A computerized system for chemical resolution of a vacuum gas oil (VGO) composition, the system comprising: one or more processors; and non-transitory computer storage media storing computer-executable instructions that, when executed by the one or more processors, cause the one or more processors to perform a method comprising: representing a FT-IR spectrum of a first VGO composition as a first weighted combination of FT-IR spectra from a database of FT-IR spectra; generating a model of composition for the first VGO composition based on the first weighted combination of FT-IR spectra; determining a first partial representation of the FT-IR spectrum of the first VGO composition as a second weighted combination of FT-IR spectra from the database of FT-IR spectra, the first partial representation being determined by partial least squares analysis, wherein the first partial representation corresponds to one or more spectral regions associated with a first compositional class, and wherein the first partial representation comprises a first leverage value and a first residual value; determining a second partial representation of the FT-IR spectrum of the first VGO composition as a third weighted combination of FT-IR spectra from the database of FT-IR spectra, the second partial representation being determined by partial least squares analysis, wherein the second partial representation comprises a second leverage value and a second residual value; calculating a combined leverage value based on at least the first leverage value and the second leverage value; calculating a combined residual value based on at least the first residual value and the second residual value; and identifying the first weighted combination of FT-IR spectra as having poor fit quality based on the combined leverage value being greater than one, the combined residual value being greater than one, or a combination thereof.

Although the present invention has been described in terms of specific embodiments, it is not so limited. Suitable alterations/modifications for operation under specific conditions should be apparent to those skilled in the art. It is therefore intended that the following claims be interpreted as covering all such alterations/modifications as fall within the true spirit/scope of the invention.

The invention claimed is:

1. A method for estimating a composition for a vacuum gas oil (VGO) composition, comprising:
representing a Fourier Transform Infrared Spectroscopy (FT-IR) spectrum of a first VGO composition as a first weighted combination of FT-IR spectra from a database of FT-IR spectra;
generating a model of composition for the first VGO composition based on the first weighted combination of FT-IR spectra;
determining a first partial representation of the FT-IR spectrum of the first VGO composition as a second weighted combination of FT-IR spectra from the database of FT-IR spectra, the first partial representation being determined by partial least squares analysis, wherein the first partial representation corresponds to one or more spectral regions associated with a first compositional class, and wherein the first partial representation comprises a first leverage value and a first residual value;
determining a second partial representation of the FT-IR spectrum of the first VGO composition as a third weighted combination of FT-IR spectra from the database of FT-IR spectra, the second partial representation being determined by partial least squares analysis, wherein the second partial representation corresponds to one or more spectral regions associated with a second compositional class, and wherein the second partial representation comprises a second leverage value and a second residual value;
calculating a combined leverage value based on at least the first leverage value and the second leverage value;
calculating a combined residual value based on at least the first residual value and the second residual value;
identifying the first weighted combination of FT-IR spectra as having poor fit quality based on the combined leverage value being greater than one, the combined residual value being greater than one, or a combination thereof.

2. The method of claim 1, wherein the first weighted combination corresponds to a linear combination of FT-IR spectra from the database of FT-IR spectra.

3. The method of claim 1, further comprising: determining a third partial representation of the FT-IR spectrum of the first VGO composition as a fourth weighted combination of FT-IR spectra from the database of FT-IR spectra, the third partial representation being determined by partial least squares analysis, wherein the third partial representation corresponds to one or more spectral regions associated with a third compositional class, and wherein the third partial representation comprises a third leverage value and a third residual value.

4. The method of claim 1, wherein the first VGO composition has an initial or T5 boiling point of at least about 650° F. (343° C.) and a final or T95 boiling point of 1050° F. (566° C.).

5. The method of claim 1, wherein at least a portion of the generating a model of composition for the first VGO composition and at least a portion of the identifying the first weighted combination of FT-IR spectra as having poor fit quality occur concurrently.

6. The method of claim 1, wherein the first compositional class and the second compositional class are selected from: n-paraffins; iso-paraffins; naphthenes; olefins; total aromatics; one-ring aromatics; two-ring aromatics; three-ring aromatics; four-ring aromatics or a combination thereof, and wherein the first compositional class and the second compositional class are different from one another.

7. The method of claim 1, wherein the one or more spectral regions of the first partial representation and the one or more spectral regions of the second partial representation are selected from: 1) about 1350 $cm^{-1}$ to about 1550 $cm^{-1}$, about 2750 $cm^{-1}$ to about 3000 $cm^{-1}$, about 4000 $cm^{-1}$ to about 4600 $cm^{-1}$, about 5400 $cm^{-1}$ to about 6000 $cm^{-1}$, or a combination thereof; 2) about 900 cm$^{-1}$ to about 1200 cm$^{-1}$, about 1300 cm$^{-1}$ to about 1600 cm$^{-1}$, about 2600 cm$^{-1}$ to about 3000 cm$^{-1}$, about 4000 cm$^{-1}$ to about 4600 cm$^{-1}$, or a combination thereof; 3) about 1450 cm$^{-1}$ to about 1550 cm$^{-1}$, about 2500 cm$^{-1}$ to about 3000 cm$^{-1}$, about 4000 cm$^{-1}$ to about 4600 cm$^{-1}$, or a combination thereof; 4) about 800 cm$^{-1}$ to about 1300 cm$^{-1}$, about 1450 cm$^{-1}$ to about 2000 cm$^{-1}$, about 3000 cm$^{-1}$ to about 3200 cm$^{-1}$, about 4000 cm$^{-1}$ to about 4600 cm$^{-1}$, or a combination thereof; 5) about 1450 cm$^{-1}$ to about 2000 cm$^{-1}$, about 3000 cm$^{-1}$ to about 3200 cm$^{-1}$, about 4000 cm$^{-1}$ to about 4600 cm$^{-1}$, or a combination thereof; 6) about 900 cm$^{-1}$ to about 1300 cm$^{-1}$, about 1550 cm$^{-1}$ to about 1750 cm$^{-1}$, about 2700 cm$^{-1}$ to about 3000 cm$^{-1}$, about 3000 cm$^{-1}$ to about 3200 cm$^{-1}$, or a combination thereof; 7) about 1000 cm$^{-1}$ to about 1100 cm$^{-1}$, about 1500 cm$^{-1}$ to about 1700 cm$^{-1}$, about 3000 cm$^{-1}$ to about 4500 cm$^{-1}$, or a combination thereof; or 8) about 900 cm$^{-1}$ to about 1000 cm$^{-1}$, about 1100 cm$^{-1}$ to about 1200 cm$^{-1}$, about 1300 cm$^{-1}$ to about 1500 cm$^{-1}$, about 1650 cm$^{-1}$ to about 1850 cm$^{-1}$, about 3100 cm$^{-1}$ to about 3300 cm$^{-1}$, about 4100 cm$^{-1}$ to about 4400 cm$^{-1}$, or a combination thereof.

8. The method of claim 1, wherein the identifying the first weighted combination of FT-IR spectra as having poor fit quality is based on the combined leverage value being greater than one and the combined residual value being greater than one.

9. The method of claim 1, wherein the model of composition for the first VGO composition comprises a relative abundance (wt. %) of one or more classes of compounds, the one or more classes of compounds comprising n-paraffins, iso-paraffins, naphthenes, aromatics, one-ring aromatics, two-ring aromatics, three-ring aromatics, and four-ring aromatics.

10. The method of claim 1, further comprising tuning the model of composition with one or more bulk properties, the one or more bulk properties comprising API gravity, viscosity, distillation temperatures, simulated distillation temperatures, sulfur content, nitrogen content, aliphatic sulfur content, basic nitrogen content, or combinations thereof.

11. A method for estimating a composition for a vacuum gas oil (VGO) composition, comprising:
representing a Fourier Transform Infrared Spectroscopy (FT-IR) spectrum of a first VGO composition as a first weighted combination of FT-IR spectra from a database of FT-IR spectra;
generating a model of composition for the first VGO composition based on the first weighted combination of FT-IR spectra;
determining a first partial representation of the FT-IR spectrum of the first VGO composition as a second weighted combination of FT-IR spectra from the database of FT-IR spectra, the first partial representation being determined by partial least squares analysis, wherein the first partial representation corresponds to a first spectral region that is associated with n-paraffins, and wherein the first partial representation comprises a first leverage value and a first residual value;
determining a second partial representation of the FT-IR spectrum of the first VGO composition as a third weighted combination of FT-IR spectra from the database of FT-IR spectra, the second partial representation being determined by partial least squares analysis, wherein the second partial representation corresponds to a second spectral region that is associated with naphthenes, and wherein the second partial representation comprises a second leverage value and a second residual value;
calculating a combined leverage value based on at least the first leverage value and the second leverage value;
calculating a combined residual value based on at least the first residual value and the second residual value;
identifying the first weighted combination of FT-IR spectra as having poor fit quality based on the combined leverage value being greater than one, the combined residual value being greater than one, or a combination thereof.

12. The method of claim 11, further comprising: determining a third partial representation of the FT-IR spectrum of the first VGO composition as a fourth weighted combination of FT-IR spectra from the database of FT-IR spectra, the third partial representation being determined by partial least squares analysis, wherein the third partial representation corresponds to a third spectral region that is associated with a compositional class selected from: iso-paraffins; aromatics; one-ring aromatics; two-ring aromatics: three-ring aromatics: or four-ring aromatics, and wherein the third partial representation comprises a third leverage value and a third residual value.

13. The method of claim 11, wherein the VGO composition has an initial or T5 boiling point of at least about 650° F. (343° C.) and a final or T95 boiling point of 1050° F. (566° C.).

14. The method of claim 11, wherein at least a portion of the generating a model of composition for the first VGO composition and at least a portion of the identifying the first weighted combination of FT-IR spectra as having poor fit quality occur concurrently.

15. The method of claim 11, wherein the identifying the first weighted combination of FT-IR spectra as having poor fit quality is based on the combined leverage value being greater than one and the combined residual value being greater than one.

16. The method of claim 11, wherein the first spectral region associated with n-paraffins comprises a wavelength region or regions of: about 1350 cm$^{-1}$ to about 1550 cm$^{-1}$, about 2750 cm$^{-1}$ to about 3000 cm$^{-1}$, about 4000 cm$^{-1}$ to about 4600 cm$^{-1}$, about 5400 cm$^{-1}$ to about 6000 cm$^{-1}$, or a combination thereof.

17. The method of claim 11, wherein the second spectral region associated with naphthenes comprises a wavelength region or regions of: about 1450 cm$^{-1}$ to about 1550 cm$^{-1}$, about 2500 cm$^{-1}$ to about 3000 cm$^{-1}$, about 4000 cm$^{-1}$ to about 4600 cm$^{-1}$, or a combination thereof.

18. The method of claim 11, wherein the model of composition for the first VGO composition comprises a relative abundance (wt. %) of one or more classes of compounds, the one or more classes of compounds comprising n-paraffins, iso-paraffins, naphthenes, aromatics, one-ring aromatics, two-ring aromatics, three-ring aromatics, and four-ring aromatics.

19. The method of claim 11, further comprising tuning the model of composition for the first VGO composition with one or more bulk properties comprising API gravity, viscosity, distillation temperatures, simulated distillation temperatures, sulfur content, nitrogen content, aliphatic sulfur content, basic nitrogen content, or combinations thereof.

20. A computerized system for chemical resolution of a vacuum gas oil (VGO) composition, the system comprising:
one or more processors; and
non-transitory computer storage media storing computer-executable instructions that, when executed by the one or more processors, cause the one or more processors to perform a method comprising:

representing a Fourier Transform Infrared Spectroscopy (FT-IR) spectrum of a first VGO composition as a first weighted combination of FT-IR spectra from a database of FT-IR spectra;

generating a model of composition for the first VGO composition based on the first weighted combination of FT-IR spectra;

determining a first partial representation of the FT-IR spectrum of the first VGO composition as a second weighted combination of FT-IR spectra from the database of FT-IR spectra, the first partial representation being determined by partial least squares analysis, wherein the first partial representation corresponds to one or more spectral regions associated with a first compositional class, and wherein the first partial representation comprises a first leverage value and a first residual value;

determining a second partial representation of the FT-IR spectrum of the first VGO composition as a third weighted combination of FT-IR spectra from the database of FT-IR spectra, the second partial representation being determined by partial least squares analysis, wherein the second partial representation corresponds to one or more spectral regions associated with a second compositional class, and wherein the second partial representation comprises a second leverage value and a second residual value;

calculating a combined leverage value based on at least the first leverage value and the second leverage value;

calculating a combined residual value based on at least the first residual value and the second residual value; and identifying the first weighted combination of FT-IR spectra as having poor fit quality based on the combined leverage value being greater than one, the combined residual value being greater than one, or a combination thereof.

* * * * *